United States Patent
Osawa et al.

(10) Patent No.: US 12,364,458 B2
(45) Date of Patent: Jul. 22, 2025

(54) ACOUSTIC LENS FOR ULTRASOUND TRANSDUCER, ULTRASOUND TRANSDUCER, ULTRASOUND PROBE, AND ULTRASOUND DIAGNOSTIC APPARATUS

(71) Applicant: FUJIFILM Corporation, Tokyo (JP)

(72) Inventors: Atsushi Osawa, Kanagawa (JP); Tatsuya Yoshihiro, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 341 days.

(21) Appl. No.: 17/702,161

(22) Filed: Mar. 23, 2022

(65) Prior Publication Data

US 2022/0211345 A1 Jul. 7, 2022

Related U.S. Application Data

(63) Continuation of application No. PCT/JP2020/039559, filed on Oct. 21, 2020.

(30) Foreign Application Priority Data

Oct. 21, 2019 (JP) .................. 2019-191863

(51) Int. Cl.
*A61B 8/00* (2006.01)
*B06B 1/06* (2006.01)
(Continued)

(52) U.S. Cl.
CPC ............ *A61B 8/4494* (2013.01); *B06B 1/067* (2013.01); *G10K 11/30* (2013.01); *H04R 17/00* (2013.01); *B06B 2201/76* (2013.01)

(58) Field of Classification Search
None
See application file for complete search history.

(56) References Cited

U.S. PATENT DOCUMENTS

| 4,651,850 A | 3/1987 | Matsuo |
| 6,560,548 B1 * | 5/2003 | Roudil ............... G01N 29/2456 73/584 |

(Continued)

FOREIGN PATENT DOCUMENTS

| JP | S58-216294 A | 12/1983 |
| JP | H03-044394 U | 4/1991 |

(Continued)

OTHER PUBLICATIONS

An Office Action; "Decision of Refusal," mailed by the Japanese Patent Office on Oct. 10, 2023, which corresponds to Japanese Patent Application No. 2021-553494 and is related to U.S. Appl. No. 17/702,161; with English language translation.

(Continued)

*Primary Examiner* — Baisakhi Roy
(74) *Attorney, Agent, or Firm* — Studebaker Brackett PLLC

(57) ABSTRACT

An acoustic lens (7) for an ultrasound transducer that is disposed in a front end portion of an ultrasound transducer (1) has a concave front surface (C1) and is formed from a base material (B) in which a plurality of fine particles (G) are dispersed. As a degree of dispersion of the fine particles (G) is higher from a central portion toward both end portions in an elevation direction, acoustic velocity is lower from the central portion toward both end portions in the elevation direction.

14 Claims, 5 Drawing Sheets

(51) Int. Cl.
*G10K 11/30* (2006.01)
*H04R 17/00* (2006.01)

(56) References Cited

U.S. PATENT DOCUMENTS

| | | | | |
|---|---|---|---|---|
| 9,970,903 | B1* | 5/2018 | Gerardi | G01N 29/032 |
| 11,610,575 | B2* | 3/2023 | Kondo | A61B 8/4483 |
| 2002/0007118 | A1 | 1/2002 | Adachi et al. | |
| 2006/0255686 | A1 | 11/2006 | Saito | |
| 2008/0132790 | A1* | 6/2008 | Burton | A61B 8/0833 |
| | | | | 600/447 |
| 2008/0303381 | A1* | 12/2008 | Yuuya | C08K 3/22 |
| | | | | 427/221 |
| 2009/0005685 | A1* | 1/2009 | Nagae | G01N 29/2418 |
| | | | | 73/632 |
| 2013/0090561 | A1 | 4/2013 | Kusukame et al. | |
| 2015/0301230 | A1* | 10/2015 | Dai | B29C 37/0053 |
| | | | | 359/601 |
| 2017/0219819 | A1* | 8/2017 | Sonoda | G02B 1/118 |
| 2017/0231578 | A1 | 8/2017 | Lading et al. | |
| 2018/0374471 | A1* | 12/2018 | Dirksen | B06B 1/0292 |
| 2019/0257943 | A1 | 8/2019 | Beers | |
| 2019/0302063 | A1* | 10/2019 | Hadimioglu | G01N 29/32 |
| 2020/0037989 | A1* | 2/2020 | Taniguchi | B06B 1/0633 |

FOREIGN PATENT DOCUMENTS

| | | |
|---|---|---|
| JP | H04-086100 A | 3/1992 |
| JP | 2005-094560 A | 4/2005 |
| JP | 2006-288977 A | 10/2006 |
| JP | 4764057 B2 | 8/2011 |
| JP | 2014-004269 A | 1/2014 |
| JP | 2019-504700 A | 2/2019 |
| WO | 2012/144117 A1 | 10/2012 |

OTHER PUBLICATIONS

The extended European search report issued by the European Patent Office on Nov. 9, 2022, which corresponds to European Patent Application No. 20879039.4-1001 and is related to U.S. Appl. No. 17/702,161.

International Search Report issued in PCT/JP2020/039559; mailed Dec. 28, 2020.

International Preliminary Report on Patentability and Written Opinion issued in PCT/JP2020/039559; issued Apr. 26, 2022.

C. M. Sayers, et al., "Ultrasonic properties of transducer backings", Ultrasonics, pp. 57-60, Mar. 1984.

Hirotada Arai, et al., "Coagulation Behavior of Suspended Particle in Liquid", Research Reports National Institute of Technology, Hachinohe College. pp. 101-107, 2016.

An Office Action; "Notice of Reasons for Refusal," mailed by the Japanese Patent Office on May 16, 2023, which corresponds to Japanese Patent Application No. 2021-553494 and is related to U.S. Appl. No. 17/702,161; with English language translation.

Communication pursuant to Article 94(3) EPC issued by the European Patent Office on May 10, 2024, which corresponds to European Patent Application No. 20879039.4-1001 and is related to U.S. Appl. No. 17/702,161.

An Office Action; "Notice of Reasons for Refusal," mailed by the Japanese Patent Office on Sep. 24, 2024, which corresponds to Japanese Patent Application No. 2021-553494 and is related to U.S. Appl. No. 17/702,161; with English language translation.

* cited by examiner

ACOUSTIC LENS FOR ULTRASOUND TRANSDUCER, ULTRASOUND TRANSDUCER, ULTRASOUND PROBE, AND ULTRASOUND DIAGNOSTIC APPARATUS

CROSS-REFERENCE TO RELATED APPLICATIONS

This application is a Continuation of PCT International Application No. PCT/JP2020/039559 filed on Oct. 21, 2020, which claims priority under 35 U.S.C. § 119(a) to Japanese Patent Application No. 2019-191863 filed on Oct. 21, 2019. The above application is hereby expressly incorporated by reference, in its entirety, into the present application.

BACKGROUND OF THE INVENTION

1. Field of the Invention

The present invention relates to an acoustic lens for an ultrasound transducer, an ultrasound transducer having the acoustic lens for an ultrasound transducer, an ultrasound probe having the ultrasound transducer, and an ultrasound diagnostic apparatus having the ultrasound probe.

2. Description of the Related Art

Hitherto, as an apparatus that obtains an image of the inside of a subject, an ultrasound diagnostic apparatus is known. In general, the ultrasound diagnostic apparatus comprises an ultrasound probe comprising an oscillator array in which a plurality of piezoelectric oscillators are arranged. In a state in which the ultrasound probe is brought into contact with a body surface of the subject, an ultrasonic beam is transmitted from the oscillator array toward the inside of the subject, and an ultrasound echo from the subject is received in the oscillator array, such that an electrical signal corresponding to the ultrasound echo is acquired. The ultrasound diagnostic apparatus electrically processes the obtained electrical signal to generate an ultrasound image of a concerned part of the subject.

In recent years, there is an increasing need to transmit ultrasonic waves having a frequency of, for example, about 12 MHz to 15 MHz to extract a tissue, such as a muscular structure or a nerve bundle, at a depth of about 5 mm to 20 mm from a body surface of a subject in an ultrasound image with high definition and to perform more detailed observation. As a method of forming an ultrasonic beam having a narrow width in an elevation direction. In such a shallow region, for example, as disclosed in JP1991-044394U (JP-H03-044394U), a method that uses an acoustic lens having a plurality of curvature radiuses in an elevation direction is known.

SUMMARY OF THE INVENTION

Note that, since the acoustic lens of JP1991-044394U (JP-H03-044394U) has a plurality of curvature radiuses in the elevation direction, in a case where the acoustic lens is brought into contact with the subject and deformed, a focal length of the acoustic lens is likely to be changed, and an ultrasonic beam may not converge at a desired depth. The acoustic lens of JP1991-044394U (JP-H03-044394U) is locally sharply thickened due to a plurality of curvature radiuses, and an ultrasonic wave propagating through the acoustic lens is likely to be locally attenuated or a place where the acoustic lens is hardly brought into contact with the subject may occur.

For this reason, in a case where an ultrasound image is captured using the acoustic lens of JP1991-044394U (JP-H03-044394U), there is a problem in that the image quality of the ultrasound image is degraded.

The present invention has been accomplished to solve such problems in the related art, and an object of the present invention is to provide an acoustic lens for an ultrasound transducer, an ultrasound transducer having the acoustic lens for an ultrasound transducer, an ultrasound probe having the ultrasound transducer, and an ultrasound diagnostic apparatus having the ultrasound probe capable of obtaining an ultrasound image having high image quality regardless of a depth.

To achieve the above-described object, the present invention provides a first acoustic lens for an ultrasound transducer that is disposed in a front end portion of an ultrasound transducer, in which the acoustic lens has a concave front surface, the acoustic lens is formed from a base material in which a plurality of fine particles are dispersed, and as a degree of dispersion of the fine particles is higher from a central portion to both end portions in an elevation direction, acoustic velocity is lower from the central portion toward both end portions in the elevation direction.

The first acoustic lens for an ultrasound transducer may have a lens part for a high acoustic velocity region disposed in the central portion of the elevation direction and lens parts for a low acoustic velocity region disposed in both end portions in the elevation direction.

The present invention provides a second acoustic lens for an ultrasound transducer that is disposed in a front end portion of an ultrasound transducer, in which the acoustic lens has a convex front surface, the acoustic lens is formed from a base material in which a plurality of fine particles are dispersed, and as a degree of dispersion of the fine particles is lower from a central portion toward both end portions in an elevation direction, acoustic velocity is higher from the central portion toward both end portions in the elevation direction.

The second acoustic lens for an ultrasound transducer may have a lens part for a low acoustic velocity region disposed in the central portion in the elevation direction and lens parts for a high acoustic velocity region disposed in both end portions in the elevation direction.

In the first acoustic lens for an ultrasound transducer and the second acoustic lens for an ultrasound transducer, it is preferable that the front surface of the acoustic lens has the same curvature radius from the central portion to both end portions in the elevation direction.

In the first acoustic lens for an ultrasound transducer and the second acoustic lens for an ultrasound transducer, it is preferable that the number of fine particles per unit volume is the same from the central portion to both end portions in the elevation direction.

The fine particles preferably have a diameter equal to or greater than 0.01 μm and equal to or smaller than 100.00 μm, and more preferably have a diameter equal to or greater than 1.00 μm and equal to or smaller than 10.00 μm.

It is preferable that the fine particles are made of iron, tungsten, alumina, zirconia, or silica.

The present invention provides an ultrasound transducer comprising a backing material, a plurality of piezoelectric oscillators arranged and formed on a surface of the backing material, an acoustic matching layer disposed on the plurality of piezoelectric oscillators, and the first acoustic lens for an ultrasound transducer or the second acoustic lens for an ultrasound transducer according to the present invention disposed on the acoustic matching layer.

The acoustic matching layer may include a first matching layer where a transmission and reception frequency of an ultrasonic wave is lower from a central portion toward both end portions in an elevation direction.

As each of the plurality of piezoelectric oscillators is thicker from the central portion toward both end portions in the elevation direction, a transmission and reception frequency of an ultrasonic wave is lower from the central portion toward both end portions in the elevation direction.

The present invention provides an ultrasound probe comprising the ultrasound transducer of the present invention.

The present invention provides an ultrasound diagnostic apparatus comprising the ultrasound probe of the present invention.

According to the present invention, the acoustic lens for an ultrasound transducer has the concave front surface and is formed from the base material in which a plurality of fine particles are dispersed, and as the degree of dispersion of the fine particles is higher from the central portion toward both end portions in the elevation direction, the acoustic velocity is lower from the central portion toward both end portions in the elevation direction or the acoustic lens for an ultrasound transducer has the convex front surface and is formed from the base material in which a plurality of fine particles are dispersed, and as the degree of dispersion of the fine particles is lower from the central portion toward both end portions in the elevation direction, the acoustic velocity is higher from the central portion toward both end portions in the elevation direction. Therefore, it is possible to obtain an ultrasound image having high image quality regardless of a depth.

DESCRIPTION OF THE PREFERRED EMBODIMENTS

Hereinafter, embodiments of the present invention will be described referring to the accompanying drawings.

The description of components described below is provided based on a representative embodiment of the present invention, but the present invention is not limited to such an embodiment.

In the specification, a numerical range represented using "to" means a range including numerical values before and after "to" as a lower limit value and an upper limit value.

In the specification, the terms "same" and "identical" include an error range allowed in the technical field.

Embodiment 1

Figure 1:
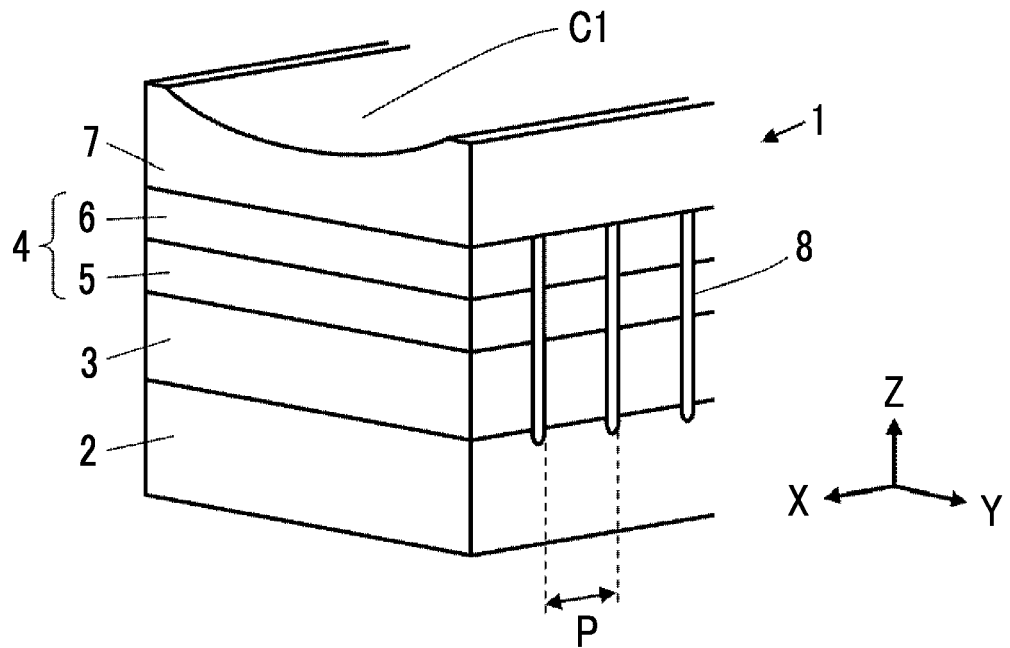
FIG. 1 is a perspective view of an ultrasound transducer having an acoustic lens for an ultrasound transducer according to Embodiment 1 of the present invention.

As shown in FIG. 1, an ultrasound transducer 1 in Embodiment 1 of the present invention comprises a backing material 2, a plurality of piezoelectric oscillators 3 arranged at an arrangement pitch P in an azimuth direction are disposed on a surface of the backing material 2, acoustic matching layers 4 are disposed on surfaces of a plurality of piezoelectric oscillators 3, respectively, and an acoustic lens 7 for an ultrasound transducer according to Embodiment 1 of the present invention is disposed on surfaces of a plurality of acoustic matching layers 4, that is, in a front end portion of the ultrasound transducer 1. Each of a plurality of acoustic matching layers 4 has a first matching layer 5 disposed on the surface of the piezoelectric oscillator 3 and a second matching layer 6 disposed on a surface of the first matching layer 5. A separation portion 8 filled with epoxy resin or the like is formed between adjacent piezoelectric oscillators 3 and between adjacent acoustic matching layers 4.

Although lead-out electrodes (not shown) are connected to a plurality of piezoelectric oscillators 3, respectively, and flexible print substrate (not shown) connected to a plurality of lead-out electrodes is disposed on a side surface of the backing material 2, these are omitted for description. Hereinafter, for description, the azimuth direction in which a plurality of piezoelectric oscillators 3 and a plurality of acoustic matching layers 4 are arranged is referred to as an X direction, and a lamination direction of the backing material 2, the piezoelectric oscillator 3, the acoustic matching layer 4, and the acoustic lens 7 for an ultrasound transducer is referred to as a Z direction, and an elevation direction perpendicular to the X direction and the Z direction is referred to as a Y direction.

The piezoelectric oscillator 3 generates an ultrasonic wave in response to a drive signal supplied from a pulser (not shown) or the like connected to the ultrasound transducer 1 and receives an ultrasound echo to output a signal based on the ultrasound echo. The piezoelectric oscillator 3 is composed by forming electrodes at both ends of a piezoelectric body consisting of, for example, piezoelectric ceramic represented by lead zirconate titanate (PZT), a polymer piezoelectric element represented by poly vinylidene di fluoride (PVDF), or piezoelectric single crystal represented by lead magnesium niobate-lead titanate (PMN-PT).

The backing material 2 supports a plurality of piezoelectric oscillators 3 and absorbs ultrasonic waves that are emitted from a plurality of piezoelectric oscillators 3 and propagate backward. The backing material 2 is formed of, for example, a rubber material, such as ferrite rubber.

The acoustic matching layer 4 matches acoustic impedance between a subject with which the ultrasound transducer 1 is brought into contact and the piezoelectric oscillator 3 to make an ultrasonic wave easily enter the subject. In general, since the acoustic impedance of the piezoelectric oscillators 3 is higher than acoustic impedance in the acoustic lens 7 for an ultrasound transducer and the subject, the acoustic matching layer 4 can be formed of a material having acoustic impedance lower than the acoustic impedance of the piezoelectric oscillator 3 and the acoustic impedance in the acoustic lens and the subject. It is desirable that, to resonate the ultrasonic wave that is emitted from the piezoelectric oscillator 3 and propagates through the first matching layer 5, to increase the intensity of the ultrasonic wave, the first matching layer 5 included in the acoustic matching layer 4 has a thickness of about ¼ of a wavelength of the ultrasonic wave propagating through the first matching layer 5. It is desirable that the second matching layer 6 also has a thickness of about ¼ of a wavelength of an ultrasonic wave propagating through the second matching layer 6 in the same manner.

The first matching layer 5 of the acoustic matching layer 4 is formed on the surface of the piezoelectric oscillator 3 and has acoustic impedance lower than the piezoelectric oscillator 3. As a material of the first matching layer 5, a resin material, such as epoxy resin or urethane resin, can be used.

The second matching layer 6 is formed on the surface of the first matching layer 5 and has acoustic impedance lower than the first matching layer 5 and higher than the acoustic lens 7 for an ultrasound transducer. As a material of the second matching layer 6, similarly to the first matching layer 5, a resin material, such as epoxy resin or urethane resin, can be used.

Figure 2:
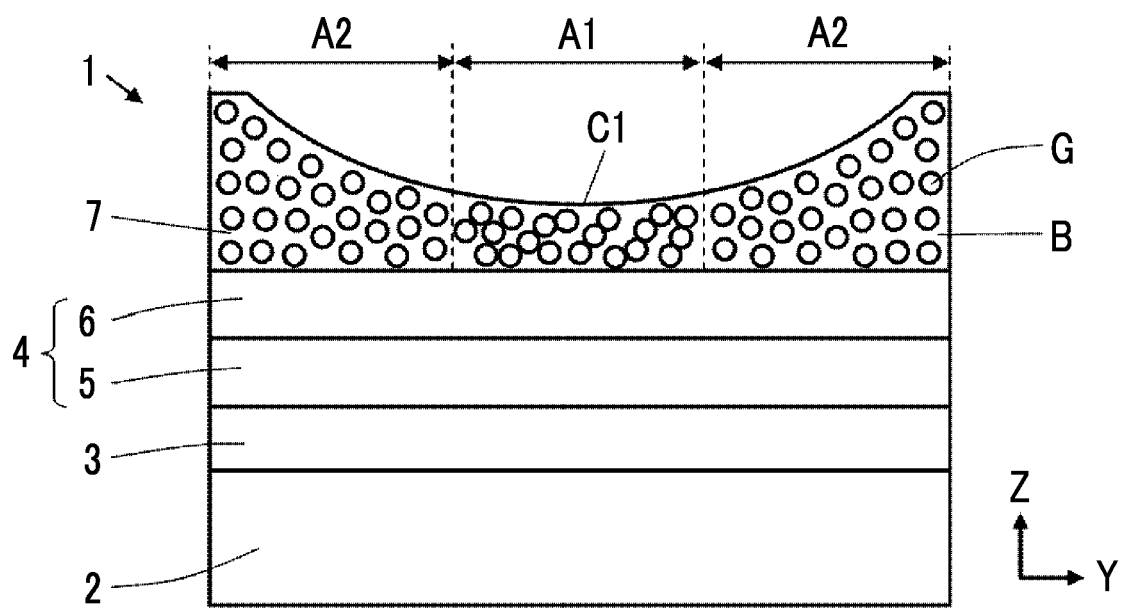
FIG. 2 is a sectional view of the ultrasound transducer having the acoustic lens for an ultrasound transducer according to Embodiment 1 of the present invention.

The acoustic lens 7 for an ultrasound transducer according to Embodiment 1 of the present invention narrows an ultrasonic beam using refraction and improves resolution in the Y direction. In the acoustic lens 7 for an ultrasound transducer, as shown in FIG. 1, a concave front surface C1 having a constant curvature radius is formed. The acoustic lens 7 for an ultrasound transducer is disposed such that the front surface C1 on a side facing away from the acoustic matching layer 4. The acoustic lens 7 for an ultrasound transducer has the concave front surface C1, whereby the acoustic lens 7 for an ultrasound transducer is formed from a material having a refractive index smaller than the subject to converge the ultrasonic beam into the subject. Here, as shown in FIG. 2, the acoustic lens 7 for an ultrasound transducer is formed from a base material B in which a plurality of fine particles G are dispersed.

The base material B is formed from, for example, a resin material, such as epoxy resin, acrylic resin, or polymethyl pentene resin, or a rubber material, such as silicon rubber. The fine particles G are formed from metal or ceramics, and as a material thereof, for example, iron, tungsten, alumina, or zirconia is used. To reduce attenuation of ultrasonic waves in the acoustic lens 7 for an ultrasound transducer, the fine particles G preferably have a diameter equal to or greater than 0.01 μm and equal to or smaller than 100.00 μm, and more preferably, have a diameter equal to or greater than 1.00 μm and equal to or smaller than 10.00 μm.

In the acoustic lens 7 for an ultrasound transducer, a degree of dispersion of the fine particles G is higher from a central portion toward both end portions in the Y direction, and the number of fine particles G per unit volume in the acoustic lens 7 for an ultrasound transducer is the same from the central portion to both end portions in the Y direction. Here, the degree of dispersion of the fine particles G is an index representing variation of a distance between adjacent fine particles G in the base material B. The degree of dispersion is high as arrangement positions of the fine particles G in the base material B are uniformly distributed, and the degree of dispersion is low as the fine particles G are locally close to each other and the arrangement positions of the fine particles G in the base material B are ununiformly distributed. In an example shown in FIG. 2, a lens part A1 for a high acoustic velocity region where the number of fine particles G in contact with or close to each other is large, that is, the degree of dispersion of the fine particles G is low is formed in the central portion in the Y direction, and lens parts A2 for a low acoustic velocity region where the number of fine particles G away from each other is large and the distribution of the arrangement positions of the fine particles G in the base material B is more uniform, that is, the degree of dispersion of the fine particles G is high are formed in both end portions in the Y direction. Here, since the number of fine particles G per unit volume is the same from the central portion to both end portions in the Y direction of the acoustic lens 7 for an ultrasound transducer, acoustic impedance of the lens part A1 for a high acoustic velocity region is substantially the same as acoustic impedance of the lens parts A2 for a low acoustic velocity region.

Incidentally, in a case where two materials having different acoustic impedance are in contact with each other and acoustic waves are transmitted through an interface between the two materials, there is known a phenomenon that a phase of the acoustic waves is influenced, and group velocity in a direction of movement of the acoustic waves decreases in the interface of the two materials. As shown in FIG. 2, in the lens part A1 for a high acoustic velocity region, since the number of fine particles G in contact with or close to each other is large, a total amount of effective interfaces between the base material B and the fine particles G is comparatively small on a propagation path of ultrasonic waves moving through the acoustic lens 7 for an ultrasound transducer in the Z direction. In the lens parts A2 for a low acoustic velocity region, since a plurality of fine particles G are more uniformly distributed, a total amount of effective interfaces between the base material B and the fine particles G is comparatively large on a propagation path of the ultrasonic waves moving through the acoustic lens 7 for an ultrasound transducer in the Z direction.

For this reason, for example, group velocity in the Z direction of the ultrasonic waves propagating through the acoustic lens 7 for an ultrasound transducer is comparatively high in the lens part A1 for a high acoustic velocity region and is comparatively low in the lens parts A2 for a low acoustic velocity region. With this, an effective refractive index of the lens part A1 for a high acoustic velocity region is comparatively small, and an effective refractive index of the lens parts A2 for a low acoustic velocity region is comparatively large. In addition, the acoustic lens 7 for an ultrasound transducer has the concave front surface C1, and a refractive index of the acoustic lens 7 for an ultrasound transducer is smaller than a refractive index of the subject. Thus, in a case where the ultrasonic waves move from the acoustic lens 7 for an ultrasound transducer to the subject through the front surface C1, the ultrasonic waves transmitted through the lens part A1 for a high acoustic velocity region are more greatly refracted toward the central portion in the Y direction of the acoustic lens 7 for an ultrasound transducer than the ultrasonic waves transmitted through the lens parts A2 for a low acoustic velocity region. For this reason, a focal length of the lens part A1 for a high acoustic velocity region is shorter than a focal length of the lens parts A2 for a low acoustic velocity region. Here, it is assumed that the focal length represents a distance between a central portion of the front surface C1 of the acoustic lens 7 for an ultrasound transducer in the Y direction and a position where a width of the ultrasonic beam is most narrowed in the Y direction.

Here, in general, it is known that, in a case where a curvature radius of a front surface of the acoustic lens is R, group velocity of ultrasonic waves propagating through the acoustic lens is V1, and group velocity of ultrasonic waves propagating through a subject is V2, a focal length F of an acoustic lens is decided by a relationship $R=F\times|(V2/V1)-1|$. With the use of the relationship, it is possible to specifically confirm that a focal length F of the lens part A1 for a high acoustic velocity region is shorter than a focal length F of the lens parts A2 for a low acoustic velocity region.

The concave front surface C1 having a constant curvature radius R is formed in the acoustic lens 7 for an ultrasound transducer, and the refractive index of the acoustic lens 7 for an ultrasound transducer is smaller than the refractive index of the subject. Thus, the group velocity V1 of the ultrasonic waves propagating through the acoustic lens 7 for an ultrasound transducer is higher than the group velocity V2 of the ultrasonic waves propagating through the subject. For this reason, a velocity ratio (V2/V1) of the group velocity V2 of the ultrasonic waves propagating through the subject to the group velocity V1 of the ultrasonic waves propagating through the acoustic lens 7 for an ultrasound transducer is greater than 0.0 and smaller than 1.0. In addition, the group velocity V1 of the ultrasonic waves propagating through the lens part A1 for a high acoustic velocity region is higher than the group velocity V1 of the ultrasonic waves propagating through the lens parts A2 for a low acoustic velocity region. Thus, the velocity ratio (V2/V1) corresponding to the lens part A1 for a high acoustic velocity region is smaller than the velocity ratio (V2/V1) corresponding to the lens parts A2 for a low acoustic velocity region.

Here, as a specific example, in a case where the velocity ratio (V2/V1) corresponding to the lens part A1 for a high acoustic velocity region is set to 0.8, and the velocity ratio (V2/V1) corresponding to the lens parts A2 for a low acoustic velocity region is set to 0.9, a relationship of $R=0.2\times F$ is obtained for the lens part A1 for a high acoustic velocity region, and a relationship of $R=0.1\times F$ is obtained for the lens parts A2 for a low acoustic velocity region. For this reason, the focal length F of the lens part A1 for a high acoustic velocity region is $5\times R$, and the focal length F of the lens parts A2 for a low acoustic velocity region is $10\times R$. In this way, it is possible to confirm that the focal length F of the lens part A1 for a high acoustic velocity region is shorter than the focal length F of the lens parts A2 for a low acoustic velocity region.

In this way, with the acoustic lens 7 for an ultrasound transducer according to Embodiment 1 of the present invention, an ultrasonic beam formed from the ultrasonic waves transmitted through the lens part A1 for a high acoustic velocity region can converge in a shallow portion of the subject, and an ultrasonic beam formed from the ultrasonic waves transmitted through the lens parts A2 for a low acoustic velocity region can converge in a deep portion of the subject. For this reason, while the front surface C1 of the acoustic lens 7 for an ultrasound transducer has the constant curvature radius R in the Y direction, it is possible to obtain an ultrasound image having high image quality regardless of a depth.

For example, in a case where piezoelectric oscillators that emit high-frequency ultrasonic waves are used as a plurality of piezoelectric oscillators 3, in particular, it is possible to obtain an ultrasound image in which a shallow portion in the subject is rendered with high definition.

Hitherto, as a method of forming an ultrasonic beam that converges in a shallow portion and has a narrow width in the Y direction, a method that uses an acoustic lens with a front surface having a plurality of curvature radiuses R in the Y direction is known. Note that, in the method, since the front surface of the acoustic lens has a plurality of curvature radiuses R in the Y direction, in a case where the acoustic lens is brought into contact with the subject and deformed, the focal length F of the acoustic lens is likely to be changed, and an ultrasonic beam may not converge at a desired depth. Furthermore, since the front surface of the acoustic lens has a plurality of curvature radiuses R, the acoustic lens is locally sharply thickened, ultrasonic waves propagating through the acoustic lens are likely to be attenuated, and a place where the acoustic lens is hardly brought into contact with the subject may occur. Such problems cause degradation of image quality of an ultrasound image.

With the acoustic lens 7 for an ultrasound transducer according to Embodiment 1 of the present invention, since the front surface C1 having the constant curvature radius R is formed in the acoustic lens 7 for an ultrasound transducer, even though the acoustic lens 7 for an ultrasound transducer is brought into contact with the subject and deformed, there is little influence of deformation, and it is possible to stably converge an ultrasonic beam conforming to a desired focal length F. Since the front surface C1 having the constant curvature radius R is formed in the acoustic lens 7 for an ultrasound transducer, the acoustic lens 7 for an ultrasound transducer is not locally sharply thickened, and it is possible to obtain an ultrasound image having high image quality regardless of a depth while reducing attenuation of the ultrasonic waves propagating through the acoustic lens 7 for an ultrasound transducer. Since the acoustic lens 7 for an ultrasound transducer is not locally sharply thickened, it is also possible to easily bring the whole of the front surface C1 of the acoustic lens 7 for an ultrasound transducer in the Y direction into contact with the subject.

The front surface C1 of the acoustic lens 7 for an ultrasound transducer is concave, and the comparatively thin lens part A1 for a high acoustic velocity region is disposed in the central portion of the acoustic lens 7 for an ultrasound transducer. Thus, even in a case where high-frequency ultrasonic waves are emitted from a plurality of piezoelectric oscillators 3, it is possible to further reduce attenuation of the high-frequency ultrasonic waves propagating through the lens part A1 for a high acoustic velocity region, and to obtain an ultrasound image having high image quality.

Next, a manufacturing method of the acoustic lens 7 for an ultrasound transducer according to Embodiment 1 of the present invention will be described.

First, surface treatment is performed on the fine particles G formed from iron, tungsten, alumina, or zirconia.

As the surface treatment on the fine particles G, for example, a treatment method including oil treatment by hydrocarbon oil, ester oil, or lanolin, silicone treatment by dimethylpolysiloxane, methylhydrogenpolysiloxane, or methylphenylpolysiloxane, fluorine compound treatment by perfluoroalkyl group-containing ester, perfluoroalkylsilane, perfluoropolyether, or a polymer having a perfluoroalkyl group, silane coupling agent treatment by 3-methacryloxypropyltrimethoxysilane or 3-glycidoxypropyltrimethoxysilane, titanate coupling agent treatment by isopropyltriisostearoyl titanate or isopropyltris(dioctylpyrophosphate) titanate, metallic soap treatment, amino acid treatment by acyl-glutamic acid, lecithin treatment by hydrogenated egg yolk lecithin, collagen treatment, polyethylene treatment, moisturizing treatment, inorganic compound treatment, mechanochemical treatment, or phosphate compound treatment by phosphoric acid, phosphorous acid, phosphate, or phosphite is used. Among the treatment methods, from a viewpoint of controlling the degree of dispersion of the fine particles G, it is preferable that phosphate compound treatment is performed.

In this case, fine particles G for a high acoustic velocity region with a large degree of surface treatment and fine particles G for a low acoustic velocity region with a small degree of surface treatment are obtained. For example, even in a case where the same surface treatment agent is used, as the amount of the surface treatment agent in the surface treatment is greater, the fine particles G with a high degree of dispersion with respect to the base material B can be obtained, and as the amount of the surface treatment agent is smaller, the fine particles G with a low degree of dispersion with respect to the base material B can be obtained. Furthermore, for example, as the number of times of the surface treatment is greater, the fine particles G with a high degree of dispersion with respect to the base material B can be obtained, and as the number of times of the surface treatment is smaller, the fine particles G with a low degree of dispersion with respect to the base material B can be obtained.

Here, to reduce attenuation of the ultrasonic waves that are emitted from the piezoelectric oscillators 3 and propagate through the acoustic lens 7 for an ultrasound transducer, the fine particles preferably have a diameter equal to or greater than 0.01 μm and equal to or smaller than 100.00 μm, and more preferably have a diameter equal to or greater than 1.00 μm and equal to or smaller than 10.00 μm. The diameter of the fine particles G can be measured as follows. First, the fine particles G sufficiently subjected to the surface treatment are added to methanol to become 0.5% by mass, and ultrasonic waves are applied for ten minutes to disperse the fine particles G in methanol. The diameter of the fine particles G can be obtained by measuring a particle size distribution of the fine particles G dispersed in methanol in such a manner is measured by a laser analysis scattering-type particle size measurement apparatus (HORIBA, Product Name: LA950V2) and calculating a volume basis median size based on the measured particle size distribution. The volume basis median size in this case is a particle size corresponding to a cumulative value of 50% in a case where the particle size distribution is represented as a cumulative distribution.

Next, as the base material B, a resin material that is cured by heating, such as epoxy resin, acrylic resin, or polymethylpentene resin, or a rubber material that is cured by heating, such as silicon rubber, is prepared, the fine particles G for a high acoustic velocity region are added to the resin material or the rubber material before curing, and the resin material or the rubber material and the fine particles G for a high acoustic velocity region are mixed by a so-called planetary mixer or the like, thereby obtaining a mixture for a high acoustic velocity region. The fine particles G for a low acoustic velocity region are added to the resin material or the rubber material before curing, and the resin material or the rubber material and the fine particles G for a low acoustic velocity region are mixed by a planetary mixer or the like, thereby obtaining a mixture for a low acoustic velocity region.

The mixture for a high acoustic velocity region before curing and the mixture for a low acoustic velocity region before curing obtained in such a manner are put in molds for molding, heated, and cured to obtain a lens member for a high acoustic velocity region and a lens member for a low acoustic velocity region. Each of the lens member for a high acoustic velocity region and the lens member for a low acoustic velocity region obtained in such a manner has a front surface curved to have the same curvature radius R. The lens member for a high acoustic velocity region is a member corresponding to the lens part A1 for a high acoustic velocity region of the acoustic lens 7 for an ultrasound transducer, and the lens member for a low acoustic velocity region is a member corresponding to the lens parts A2 for a low acoustic velocity region.

Finally, the lens members for a low acoustic velocity region are adhered to both ends of the lens member for a high acoustic velocity region using an adhesive, such as an epoxy adhesive, whereby the acoustic lens 7 for an ultrasound transducer shown in FIGS. 1 and 2 is obtained.

Incidentally, as an acoustic lens for forming an ultrasonic beam having a narrow width in the Y direction, an acoustic lens in which a front surface having a plurality of curvature radiuses R in the Y direction is formed is known. In general, an ultrasound transducer that emits high-frequency ultrasonic waves of 10 MHz to 15 MHz often has a small size, and it is difficult to manufacture an acoustic lens in which a front surface having a plurality of curvature radiuses R in the Y direction is formed, conforming to the ultrasound transducer having a small size.

In the acoustic lens 7 for an ultrasound transducer according to Embodiment 1 of the present invention, since the front surface C1 having the constant curvature radius R is formed, for example, even in a case where the ultrasound transducer 1 has a small size corresponding to oscillation of high-frequency ultrasonic waves, the acoustic lens 7 for an ultrasound transducer can be easily manufactured conforming to the size of the ultrasound transducer 1.

Figure 3:
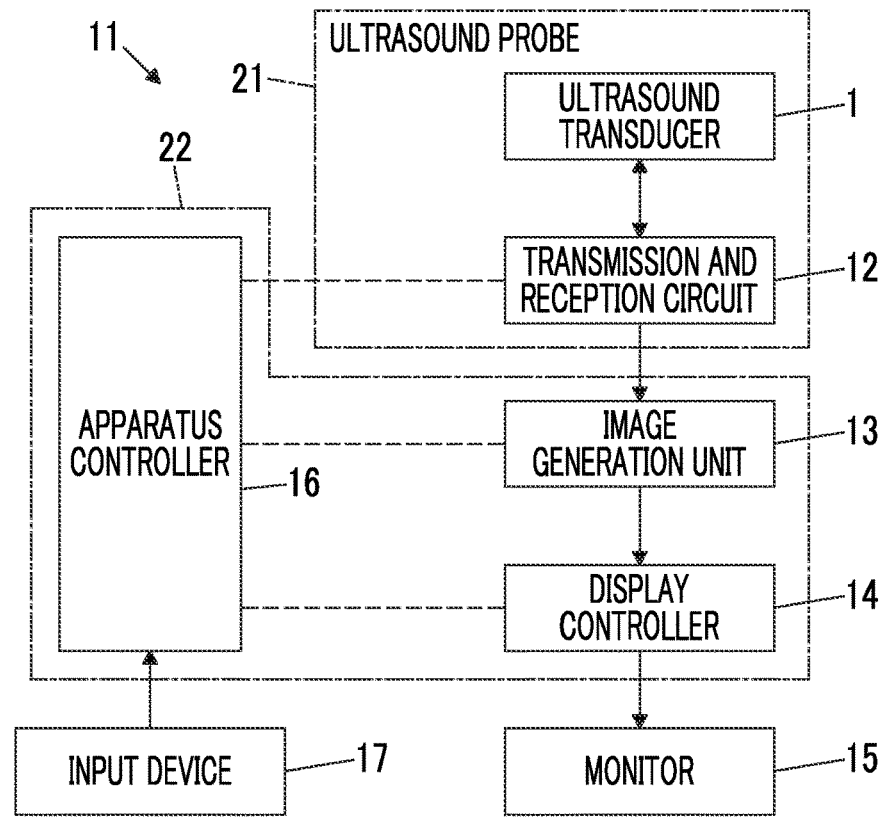
FIG. 3 is a block diagram showing the configuration of an ultrasound diagnostic apparatus having the ultrasound transducer in Embodiment 1 of the present invention.

Next, an ultrasound diagnostic apparatus having the ultrasound transducer 1 according to Embodiment 1 of the present invention will be described. As shown in FIG. 3, in an ultrasound diagnostic apparatus 11, a transmission and reception circuit 12, an image generation unit 13, a display controller 14, and a monitor 15 are sequentially connected to the ultrasound transducer 1. An apparatus controller 16 is connected to the transmission and reception circuit 12, the image generation unit 13, and the display controller 14. An input device 17 is connected to the apparatus controller 16. A memory (not shown) is connected to the apparatus controller 16.

The ultrasound diagnostic apparatus 11 comprises an ultrasound probe 21 including the ultrasound transducer 1 and the transmission and reception circuit 12. A processor 22 for the ultrasound diagnostic apparatus 11 is configured by the image generation unit 13, the display controller 14, and the apparatus controller 16.

Figure 4:
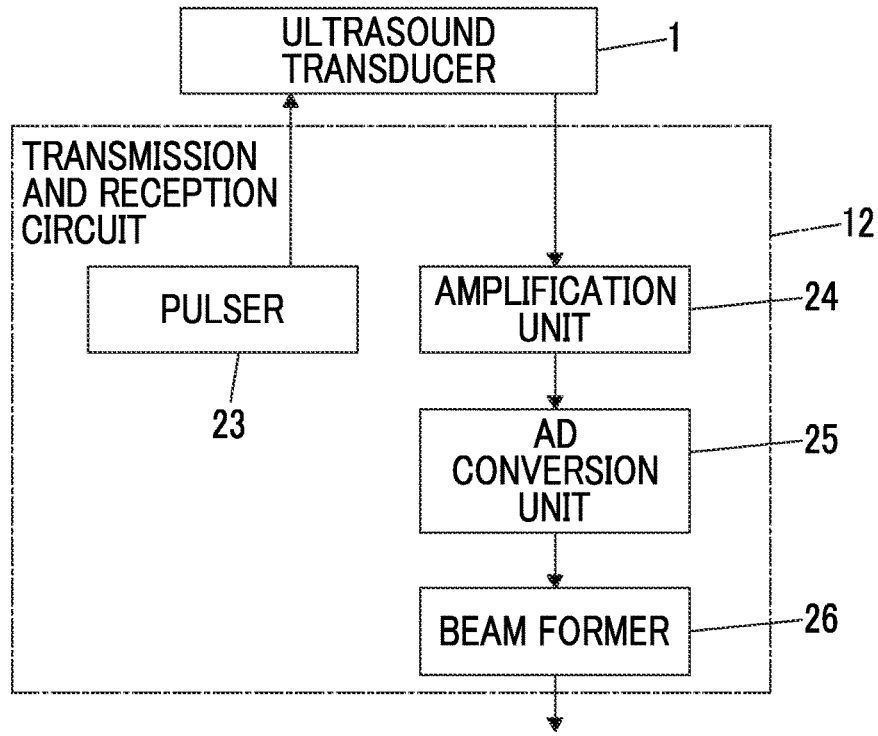
FIG. 4 is a block diagram showing the internal configuration of a transmission and reception circuit in Embodiment 1 of the present invention.

The transmission and reception circuit 12 transmits ultrasonic waves from the ultrasound transducer 1 and generates sound ray signals based on reception signals acquired by the ultrasound transducer 1 under the control of the apparatus controller 16. As shown in FIG. 4, the transmission and reception circuit 12 has a pulser 23 connected to the ultrasound transducer 1, an amplification unit 24, an analog digital (AD) conversion unit 25, and a beam former 26 sequentially connected in series from the ultrasound transducer 1.

The pulser 23 includes, for example, a plurality of pulse generators, adjusts a delay amount of each of drive signals based on a transmission delay pattern selected in response to a control signal from the apparatus controller 16 such that ultrasonic waves transmitted from a plurality of piezoelectric oscillators 3 of the ultrasound transducer 1 form an ultrasonic beam, and supplies the drive signals to a plurality of piezoelectric oscillators 3. In this way, in a case where a pulsed or continuous-wave voltage is applied to the electrodes of the piezoelectric oscillators 3, the piezoelectric oscillators 3 expand and contract, a pulsed or continuous-wave ultrasonic wave is generated from each of the piezoelectric oscillators 3, and an ultrasonic beam is formed from a combined wave of the ultrasonic waves.

The transmitted ultrasonic beam is reflected by, for example, a tissue in the subject and propagates toward the ultrasound transducer 1 of the ultrasound probe 21. Each of the piezoelectric oscillators 3 of the ultrasound transducer 1 expands and contract with reception of an ultrasound echo propagating toward the ultrasound transducer 1 in this manner, generates a reception signal that is an electrical signal, and outputs the reception signal to the amplification unit 24.

The amplification unit 24 amplifies the signal input from each of the piezoelectric oscillators 3 of the ultrasound transducer 1 and transmits the amplified signal to the AD conversion unit 25. The AD conversion unit 25 converts the signal transmitted from the amplification unit 24 into digital reception data and transmits the reception data to the beam former 26. The beam former 26 performs so-called reception focus processing by giving a delay to each piece of reception data converted by the AD conversion unit 25 conforming to acoustic velocity or distribution of acoustic velocity set based on a reception delay pattern selected in response to a control signal from the apparatus controller 16 and performing addition. With the reception focus processing, each piece of reception data converted in the AD conversion unit 25 is subjected to phasing addition, and a sound ray signal in which a focus of the ultrasound echo is narrowed is acquired.

Figure 5:
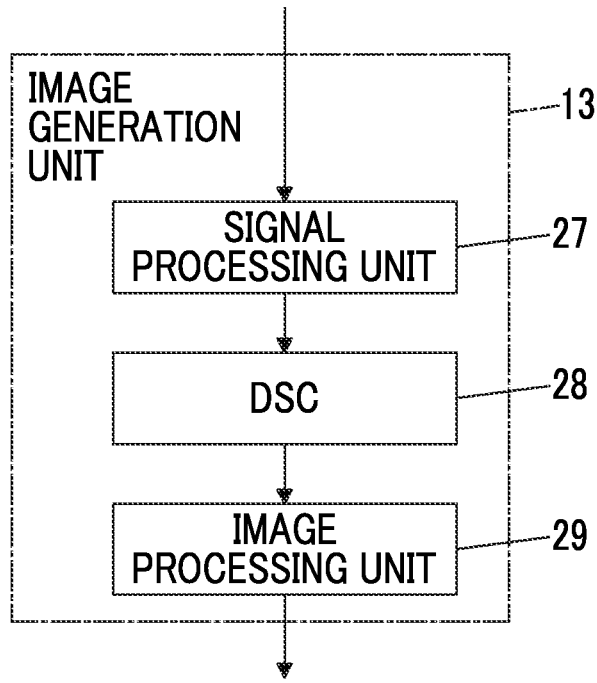
FIG. 5 is a block diagram showing the internal configuration of an image generation unit in Embodiment 1 of the present invention.

As shown in FIG. 5, the image generation unit 13 has a configuration in which a signal processing unit 27, a digital scan converter (DSC) 28, and an image processing unit 29 are sequentially connected in series.

The signal processing unit 27 performs correction of attenuation of on the sound ray signal generated by the beam former 26 of the transmission and reception circuit 12 due to a distance depending on a depth of a reflection position of an ultrasonic wave, and then, executes envelope detection processing, thereby generating a B mode image signal that is tomographic image information regarding a tissue in the subject.

The DSC 28 converts (raster-converts) the B mode image signal generated in the signal processing unit 27 into an image signal conforming to a normal television signal scanning system.

The image processing unit 29 executes various kinds of necessary image processing, such as gradation processing, on the B mode image signal input from the DSC 28, and then, outputs the B mode image signal to the display controller 14. In the present invention, the B mode image signal subjected to the image processing by the image processing unit 29 is simply referred to as an ultrasound image.

The display controller 14 executes predetermined processing on the ultrasound image generated by the image generation unit 13 and displays the ultrasound image on the monitor 15 under the control of the apparatus controller 16.

The monitor 15 displays the ultrasound image generated by the image generation unit 13 under the control of the display controller 14, and includes, for example, a liquid crystal display (LCD) or an organic electroluminescence display (organic EL display).

The apparatus controller 16 performs control of each unit of the ultrasound diagnostic apparatus 11 based on a control program stored in advance.

The input device 17 is provided for the user to perform an input operation, and can comprise a keyboard, a mouse, a trackball, a touch pad, a touch panel, and the like.

Though not shown, a memory that is connected to the apparatus controller 16 stores the control program of the ultrasound diagnostic apparatus 11, and the like, and as the memory, a recording medium, such as a flash memory, a hard disc drive (HDD), a solid state drive (SSD), a flexible disc (FD), a magneto-optical disc (MO disc)), a magnetic tape (MT), a random access memory (RAM), a compact disc (CD), a digital versatile disc (DVD), a secure digital card (SD card), or a universal serial bus memory (USB memory), a server, or the like can be used.

Although the processor 22 having the image generation unit 13, the display controller 14, and the apparatus controller 16 is configured with a central processing unit (CPU) and a control program causing the CPU to execute various kinds of processing, the processor 22 may be configured using a field programmable gate array (FPGA), a digital signal processor (DSP), an application specific integrated circuit (ASIC), a graphics processing unit (GPU), and other integrated circuits (ICs) or may be configured by combining such ICs.

The image generation unit 13, the display controller 14, and the apparatus controller 16 of the processor 22 may be configured to be partially or wholly integrated into one CPU or the like.

Since the ultrasound diagnostic apparatus 11 in Embodiment 1 of the present invention comprises the ultrasound transducer 1 having the acoustic lens 7 for an ultrasound transducer according to Embodiment 1 of the present invention, it is possible to obtain an ultrasound image having high image quality regardless of a depth. In particular, in a case where comparatively high-frequency ultrasonic waves are emitted from the ultrasound transducer 1, it is possible to obtain an ultrasound image where a region of a shallow portion is rendered with high definition.

While the degree of dispersion of the fine particles G with respect to the base material B in the acoustic lens 7 for an ultrasound transducer is adjusted by performing the surface treatment on the fine particles G, a method of adjusting the degree of dispersion of the fine particles G is not limited to the surface treatment. For example, the degree of dispersion of the fine particles G in the base material B can be changed by changing a method of mechanically mixing the fine particles G in the base material B. For example, it is possible to decrease the degree of dispersion of the fine particles G by mixing the fine particles G in the base material B using a so-called propeller type mixer, compared to a case where the fine particles G are mixed using the planetary mixer. For this reason, in a case of producing the mixture for a high acoustic velocity region, the fine particles G can be mixed in the base material B using the propeller type mixer, and in a case of producing the mixture for a low acoustic velocity region, the fine particles G can be mixed in the base material B using the planetary mixer.

For example, the degree of dispersion of the fine particles G can be changed by changing a time for which the fine particles G are mixed in the base material B.

For example, the degree of dispersion of the fine particles G can be changed by changing a time required for curing the base material B. For example, in a case where a temperature for heating the mixture of the base material B and the fine particles G decreases to extend the time required for curing the base material B, the degree of dispersion of the fine particles G can be decreased, and in a case where the temperature for heating the mixture of the base material B and the fine particles G increases to reduce the time required for curing the base material B, the degree of dispersion of the fine particles G can be increased.

Although an example where the acoustic lens 7 for an ultrasound transducer is configured by two kinds of regions of the lens part A1 for a high acoustic velocity region and the lens parts A2 for a low acoustic velocity region has been shown, in a case where the degree of dispersion of the fine particles G in the base material B is higher from the central portion toward both end portions in the Y direction, the acoustic lens 7 for an ultrasound transducer may be configured by three kinds or more of regions having different degrees of dispersion of the fine particles G. Alternatively, the acoustic lens 7 for an ultrasound transducer may be configured such that the degree of dispersion of the fine particles G in the base material B is continuously higher from the central portion toward both end portions of the acoustic lens 7 for an ultrasound transducer in the Y direction. With this, it is possible to obtain an ultrasound image having more uniform image quality.

Although it has been described that the number of the fine particles G per unit volume in the lens part A1 for a high acoustic velocity region and the number of fine particles G per unit volume in the lens parts A2 for a low acoustic velocity region are the same, the number of the fine particles G per unit volume in the lens part A1 for a high acoustic velocity region and the number of fine particles G per unit volume in the lens parts A2 for a low acoustic velocity region may be subjected to fine adjustment to regulate the acoustic impedance of the lens part A1 for a high acoustic velocity region and the lens parts A2 for a low acoustic velocity region.

Embodiment 2

Although the acoustic lens 7 for an ultrasound transducer according to Embodiment 1 of the present invention has the concave front surface C1, the acoustic lens 7 for an ultrasound transducer may have a convex front surface.

Figure 6:
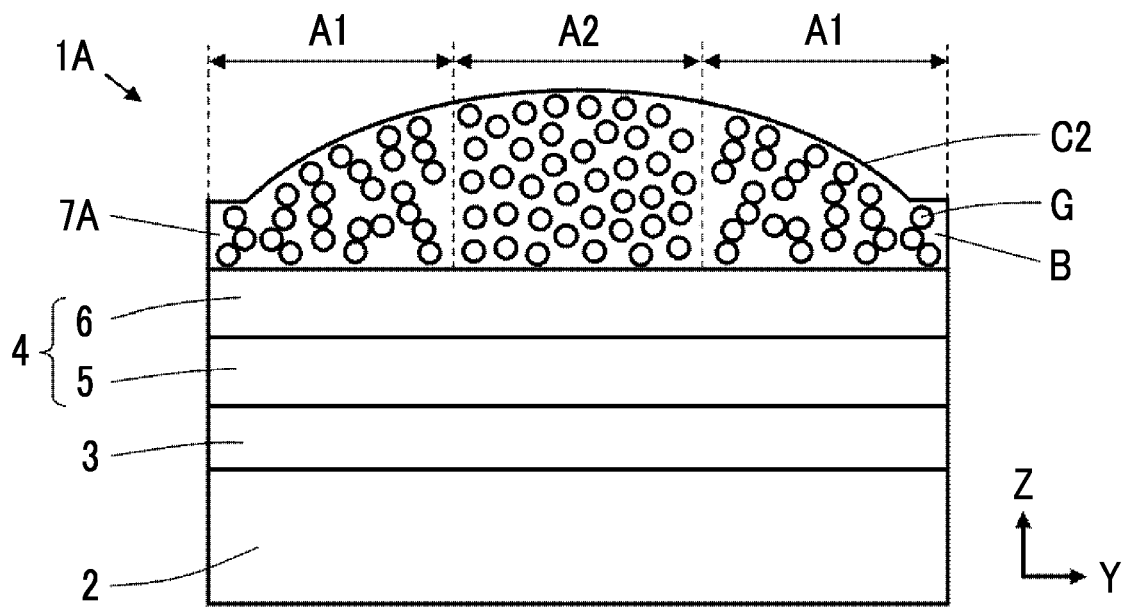
FIG. 6 is a sectional view of an ultrasound transducer having an acoustic lens for an ultrasound transducer according to Embodiment 2 of the present invention.

As shown in FIG. 6, an ultrasound transducer 1A in Embodiment 2 of the present invention comprises an acoustic lens 7A for an ultrasound transducer instead of the acoustic lens 7 for an ultrasound transducer in the ultrasound transducer 1 in Embodiment 1 shown in FIGS. 1 and 2.

While the acoustic lens 7A for an ultrasound transducer according to Embodiment 2 of the present invention is formed from the base material B in which a plurality of fine particles G are dispersed, in the same manner as the acoustic lens 7 for an ultrasound transducer of Embodiment 1, the acoustic lens 7A for an ultrasound transducer according to Embodiment 2 of the present invention has a convex front surface C2 having a constant curvature radius R, has a lens part A2 for a low acoustic velocity region where the degree of dispersion of the fine particles G is high, in the central portion of the acoustic lens 7A for an ultrasound transducer in the Y direction, and has lens parts A1 for a high acoustic velocity region where the degree of dispersion of the fine particles G is low, in both end portions of the acoustic lens 7A for an ultrasound transducer in the Y direction. In this way, in the acoustic lens 7A for an ultrasound transducer, the degree of dispersion of the fine particles G is lower from the central portion toward both end portions in the Y direction. The number of fine particles G per unit volume in the acoustic lens 7A for an ultrasound transducer is the same from the central portion to both end portions in the Y direction. For this reason, the acoustic impedance of the lens part A2 for a low acoustic velocity region and the acoustic impedance of the lens parts A1 for a high acoustic velocity region are substantially the same.

The acoustic lens 7A for an ultrasound transducer is formed of a material having a refractive index greater than the subject to converge an ultrasonic beam into the subject.

Here, group velocity V1 in the Z direction of ultrasonic waves propagating through the acoustic lens 7A for an ultrasound transducer is comparatively low than in the lens part A2 for a low acoustic velocity region disposed in the central portion in the Y direction and is comparatively high in the lens parts A1 for a high acoustic velocity region disposed in both end portions in the Y direction. Thus, an effective refractive index of the lens part A2 for a low acoustic velocity region is comparatively large, and an effective refractive index of the lens parts A1 for a high acoustic velocity region is comparatively small. The acoustic lens 7A for an ultrasound transducer has the convex front surface C2, and the refractive index of the acoustic lens 7A for an ultrasound transducer is greater than the refractive index of the subject. Thus, in a case where the ultrasonic waves move from the acoustic lens 7A for an ultrasound transducer to the subject through the front surface C2, the ultrasonic waves transmitted through the lens part A2 for a low acoustic velocity region are more greatly refracted toward the central portion of the acoustic lens 7A for an ultrasound transducer in the Y direction than the ultrasonic waves transmitted through the lens parts A1 for a high acoustic velocity region. For this reason, a focal length F of the lens part A2 for a low acoustic velocity region is shorter than a focal length F of the lens parts A1 for a high acoustic velocity region.

The convex front surface C2 having the constant curvature radius R is formed in the acoustic lens 7A for an ultrasound transducer, and the refractive index of the acoustic lens 7A for an ultrasound transducer is greater than the refractive index of the subject. Thus, the group velocity V1 of the ultrasonic waves propagating through the acoustic lens 7A for an ultrasound transducer is lower than group velocity V2 of ultrasonic waves propagating through the subject. For this reason, a velocity ratio (V2/V1) of the group velocity V2 propagating through the subject to the group velocity V1 of the ultrasonic waves propagating through the acoustic lens 7A for an ultrasound transducer is greater than 1.0. The group velocity V1 of the ultrasonic waves propagating through the lens part A2 for a low acoustic velocity region is lower than the group velocity V1 of the ultrasonic waves propagating through the lens parts A1 for a high acoustic velocity region. Thug, the velocity ratio (V2/V1) corresponding to the lens part A2 for a low acoustic velocity region is greater than the velocity ratio (V2/V1) corresponding to the lens parts A1 for a high acoustic velocity region.

Here, as a specific example, in a case where the velocity ratio (V2/V1) corresponding to the lens part A2 for a low acoustic velocity region is set to 1.2, and the velocity ratio (V2/V1) corresponding to the lens parts A1 for a high acoustic velocity region is set to 1.1, from a relationship of $R=F\times|(V2/V1)-1|$, a relationship of $R=0.2\times F$ is obtained for the lens part A2 for a low acoustic velocity region, and a relationship of $R=0.1\times F$ is obtained for the lens parts A1 for a high acoustic velocity region. For this reason, the focal length F of the lens part A2 for a low acoustic velocity region is 5×R, and the focal length F of the lens parts A1 for a high acoustic velocity region is 10×R. In this way, it is possible to confirm that the focal length F of the lens part A2 for a low acoustic velocity region is shorter than the focal length F of the lens parts A1 for a high acoustic velocity region.

In this way, with the acoustic lens 7A for an ultrasound transducer according to Embodiment 2 of the present invention, an ultrasonic beam formed from the ultrasonic waves transmitted through the lens part A2 for a low acoustic velocity region can converge in a shallow portion of the subject, and an ultrasonic beam formed from the ultrasonic waves transmitted through the lens parts A1 for a high acoustic velocity region can converge in a deep portion of the subject. For this reason, it is possible to obtain an ultrasound image having high image quality regardless of a depth while the front surface C2 of the acoustic lens 7A for an ultrasound transducer has the constant curvature radius R in the Y direction.

For example, in a case where piezoelectric oscillators that emit high-frequency ultrasonic waves are used as a plurality of piezoelectric oscillators 3, in particular, it is possible to obtain an ultrasound image in which a shallow portion in the subject is rendered with high definition.

Since the front surface C2 having the constant curvature radius R is formed in the acoustic lens 7A for an ultrasound transducer, even though the acoustic lens 7A for an ultrasound transducer is brought into contact with the subject and deformed, there is little influence of deformation, and it is possible to stably converge an ultrasonic beam conforming to a desired focal length F. Since the front surface C2 having the constant curvature radius R is formed in the acoustic lens 7A for an ultrasound transducer, the acoustic lens 7A for an ultrasound transducer is not locally sharply thickened, and it is possible to obtain an acoustic lens 7A for an ultrasound image having high image quality regardless of a depth while reducing attenuation of the ultrasonic waves propagating through the ultrasound transducer. In addition, since the acoustic lens 7A for an ultrasound transducer is not locally sharply thickened, it is possible to easily bring the whole of the front surface C2 of the acoustic lens 7A for an ultrasound transducer in the Y direction into contact with the subject.

Although an example where the acoustic lens 7A for an ultrasound transducer is configured by two kinds of regions of the lens part A2 for a low acoustic velocity region and the lens parts A1 for a high acoustic velocity region has been shown, in a case where the degree of dispersion of the fine particles G in the base material B is lower from the central portion toward both end portions in the Y direction, the acoustic lens 7A for an ultrasound transducer may be configured by three kinds or more of regions having different degrees of dispersion of the fine particles G. Alternatively, the acoustic lens 7A for an ultrasound transducer may be configured such that the degree of dispersion of the fine particles G in the base material B is continuously lower from the central portion toward both end portions of the acoustic lens 7A for an ultrasound transducer in the Y direction. With this, it is possible to obtain an ultrasound image having more uniform image quality.

Embodiment 3

Although the acoustic lens 7 for an ultrasound transducer according to Embodiment 1 is formed from the base material B in which a plurality of fine particles G are dispersed, a layer formed from the base material B in which a plurality of fine particles G are dispersed may be included in the acoustic matching layer 4.

Figure 7:
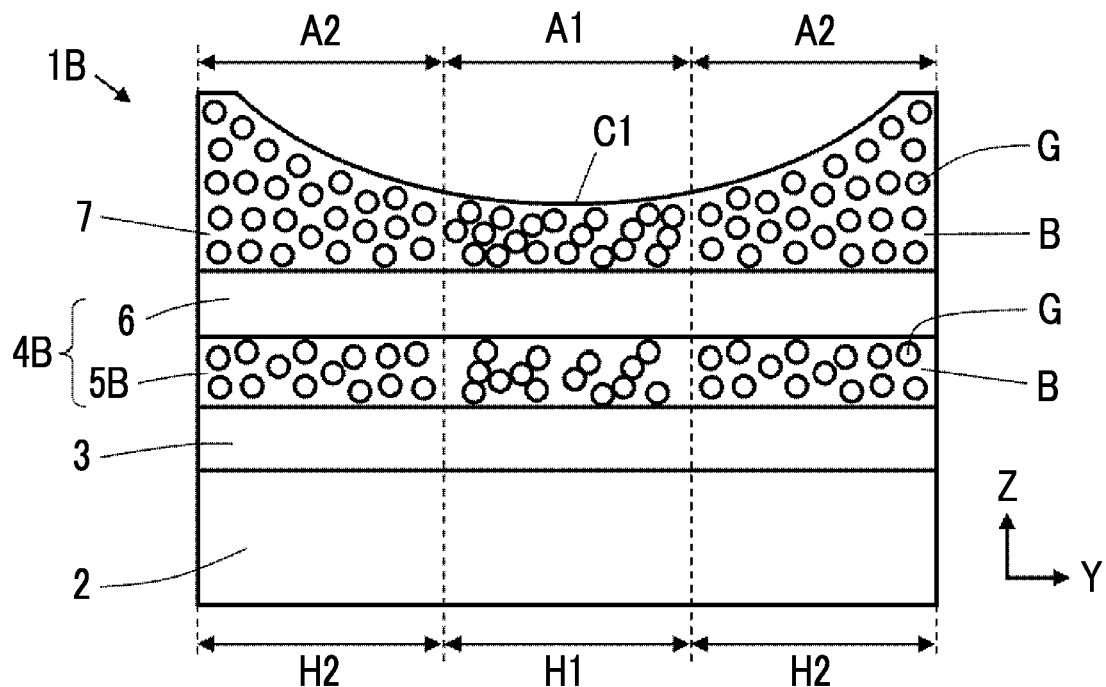
FIG. 7 is a sectional view of an ultrasound transducer in Embodiment 3 of the present invention.

As shown in FIG. 7, an ultrasound transducer 1B in Embodiment 3 comprises an acoustic matching layer 4B instead of the acoustic matching layer 4 in the ultrasound transducer 1 in Embodiment 1 shown in FIG. 2. The acoustic matching layer 4B has a first matching layer 5B instead of the first matching layer 5 in the acoustic matching layer 4 in Embodiment 1. As shown in FIG. 7, the first matching layer 5B is formed from the base material B in which a plurality of fine particles G are dispersed.

In the first matching layer 5B, the degree of dispersion of the fine particles G is higher from the central portion toward both end portions in the Y direction, and the number of fine particles G per unit volume in the first matching layer 5 is the same from the central portion to both end portions in the Y direction. In an example shown in FIG. 7, a matching part H1 for a high frequency region where the degree of dispersion of the fine particles G is low is formed in the central portion in the Y direction, and matching parts H2 for a low frequency region where the degree of dispersion of the fine particles G is high are formed in both end portions in the Y direction. Here, the matching part H1 for a high frequency region is formed at a position in the Y direction corresponding to the lens part A1 for a high acoustic velocity region of the acoustic lens 7 for an ultrasound transducer, and the matching parts H2 for a low frequency region are formed at positions in the Y direction corresponding to the lens parts A2 for a low acoustic velocity region of the acoustic lens 7 for an ultrasound transducer. Since the number of the fine particles G per unit volume is the same from the central portion to both end portions of the first matching layer 5B in the Y direction, acoustic impedance of the matching part H1 for a high frequency region and acoustic impedance of the matching parts H2 for a low frequency region are substantially the same.

Here, there is known a relationship of $V=Q \times W$ where group velocity of an acoustic velocity is V, a frequency is Q, and a wavelength is W. Ultrasonic waves having a constant wavelength W are enhanced under a resonance condition due to a thickness of the first matching layer 5B. Thus, it is understood that, in a case where the wavelength W is made constant, since group velocity V of the ultrasonic waves propagating through the matching part H1 for a high frequency region of the first matching layer 5B is comparatively high, the frequency Q is high, and since the group velocity V of the ultrasonic waves propagating through the matching parts H2 for a low frequency region is comparatively low, the frequency is low.

Since the matching part H1 for a high frequency region is disposed in the central portion of the acoustic matching layer 4B in the Y direction, the matching part H1 for a high frequency region has a comparatively wide opening width compared to a full width of the acoustic matching layer 4 in the Y direction. On the other hand, since the matching parts H2 for a low frequency region are disposed in both end portions of the acoustic matching layer 4B, the matching parts H2 for a low frequency region have a comparatively wide opening width. For this reason, a width in the Y direction of an ultrasonic beam in a case where the ultrasonic waves transmitted through the matching part H1 for a high frequency region are converged by the acoustic lens 7 for an ultrasound transducer is comparatively narrow, and a width in the Y direction of an ultrasonic beam in a case where the ultrasonic waves transmitted through the matching parts H2 for a low frequency region are converged by the acoustic lens 7 for an ultrasound transducer is comparatively wide.

Accordingly, an ultrasonic beam formed from the ultrasonic waves transmitted through the matching part H1 for a high frequency region of the first matching layer 5B and the lens part A1 for a high acoustic velocity region of the acoustic lens 7 for an ultrasound transducer has a comparatively high frequency Q and has a comparatively narrow width in the Y direction and converges conforming to a short focal length F. An ultrasonic beam formed from the ultrasonic waves transmitted through the matching parts H2 for a low frequency region of the first matching layer 5B and the lens parts A2 for a low acoustic velocity region of the acoustic lens 7 for an ultrasound transducer has a comparatively low frequency Q and converges conforming to a long focal length F.

With this, with the ultrasound transducer 1B in Embodiment 3 of the present invention, it is possible to obtain an ultrasound image having higher image quality regardless of a depth.

Figure 8:
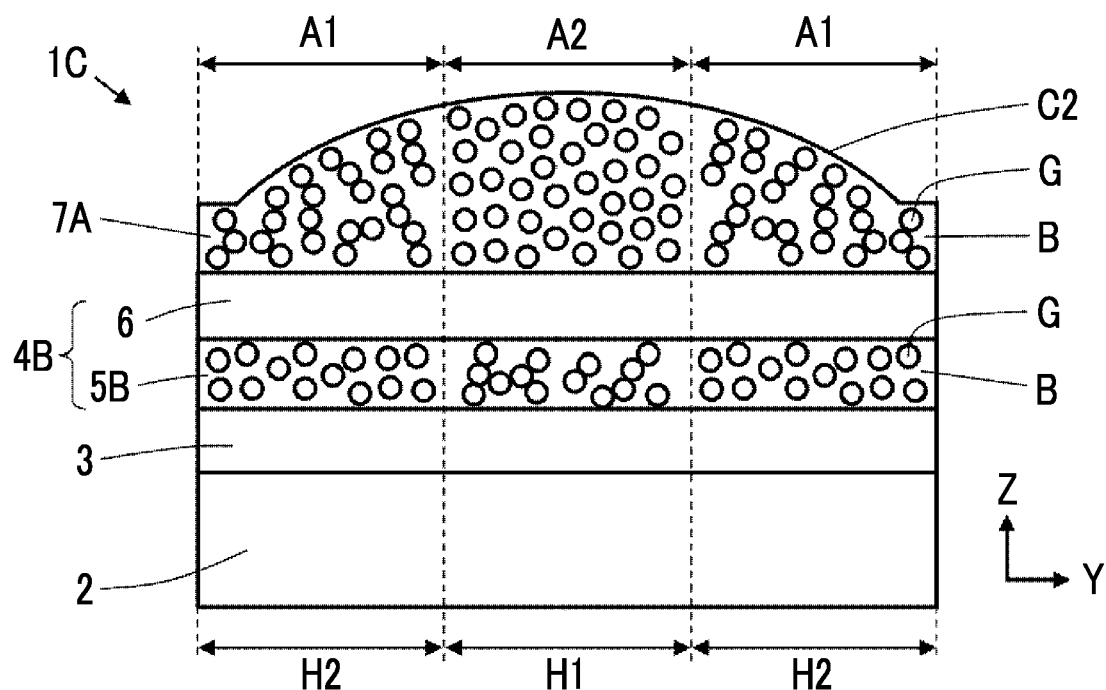
FIG. 8 is a sectional view of an ultrasound transducer in a modification example of Embodiment 3 of the present invention.

Although it has been shown that an aspect of Embodiment 3 is applied to the ultrasound transducer 1 in Embodiment 1, the aspect of Embodiment 3 can be applied to the ultrasound transducer 1A in Embodiment 2 in the same manner. For example, as shown in FIG. 8, an ultrasound transducer 1C in a modification example of Embodiment 3 comprises the first matching layer 5B instead of the first matching layer 5 in the ultrasound transducer 1A in Embodiment 2 shown in FIG. 6.

In this case, the ultrasonic beam formed from the ultrasonic waves transmitted through the matching part H1 for a high frequency region of the first matching layer 5B and the lens part A2 for a low acoustic velocity region of the acoustic lens 7A for an ultrasound transducer has a comparatively high frequency Q, has a comparatively narrow width in the Y direction, and converges conforming to a short focal length F. The ultrasonic beam formed from the ultrasonic waves transmitted through the matching parts H2 for a low frequency region of the first matching layer 5B and the lens parts A1 for a high acoustic velocity region of the acoustic lens 7A for an ultrasound transducer has a comparatively low frequency Q and converges conforming to a long focal length F.

In this way, with the ultrasound transducer 1C in the modification example of Embodiment 3 of the present invention, in the same manner as the ultrasound transducer 1B in Embodiment 3, it is possible to obtain an ultrasound image having higher image quality regardless of a depth.

A length of the matching part H1 for a high frequency region in the Y direction is longer than a length of each of the matching parts H2 for a low frequency region in the Y direction, whereby it is possible to increase a proportion of ultrasonic waves transmitted and received through the matching part H1 for a high frequency region. While ultrasonic waves having a higher frequency are more easily attenuated, the matching part H1 for a high frequency region is made long in the Y direction, whereby even though comparatively high-frequency ultrasonic waves are attenuated in the subject, it is possible to sufficiently secure the amount of ultrasound echo that is received through the matching part H1 for a high frequency region, to restrain degradation of brightness of an ultrasound image of a comparatively shallow portion. With this, it is possible to obtain an ultrasound image having more uniform image quality.

In this case, for example, it is preferable that the length of the matching part H1 for a high frequency region in the Y direction is longer than ½ of a total length of the first matching layer 5B in the Y direction. Specifically, for example, the length of the matching part H1 for a high frequency region in the Y direction may be two times or three times greater than the length of each of the matching parts H2 for a low frequency region in the Y direction.

Although an example where the first matching layer 5B is configured by two kinds of regions of the matching part H1 for a high frequency region and the matching parts H2 for a low frequency region has been shown, in a case where the degree of dispersion of the fine particles G in the base material B is higher from the central portion toward both end portions in the Y direction such that the transmission and reception frequency of the ultrasonic waves is lower from the central portion toward both end portions in the Y direction, the first matching layer 5B may be configured by three kinds or more of regions having different degrees of dispersion of the fine particles G. Alternatively, the first matching layer 5B may be configured such that the degree of dispersion of the fine particles G in the base material B is continuously higher from the central portion toward both end portions of the first matching layer 5B in the Y direction. For this reason, it is possible to obtain an ultrasound image having more uniform image quality.

For example, the first matching layer 5B may be configured by a multi-layered structure consisting of a plurality of layers having different acoustic impedance. For example, a layer where a plurality of fine particles G are dispersed in the base material B having higher acoustic impedance can be disposed toward the piezoelectric oscillator 3 in the Z direction, and a layer where a plurality of fine particles G are dispersed in the base material B having lower acoustic impedance can be disposed toward the second matching layer 6 in the Z direction. Since the acoustic impedance can be increased more as the number of fine particles G per unit volume dispersed in the base material B is greater, for example, a layer where the number of fine particles G per unit volume dispersed in the base material B is greater can be disposed toward the piezoelectric oscillator 3 in the Z direction, and a layer where the number of fine particles G per unit volume dispersed in the base material B is smaller can be disposed toward the second matching layer 6 in the Z direction.

In this way, the first matching layer 5B has a multi-layered structure having different acoustic impedance, whereby it is possible to match acoustic impedance between the subject into which the ultrasound transducer 1B is brought into contact and the piezoelectric oscillator 3 with high accuracy, and to make an ultrasonic wave easily enter the subject.

Though not shown, the ultrasound diagnostic apparatus 11 having the ultrasound transducer 1B of Embodiment 3 or the ultrasound transducer 1C can comprise a so-called low-pass filter and a so-called high-pass filter and can execute filter processing depending on a depth, for example, on the reception data digitized by the AD conversion unit 25 using the low-pass filter and the high-pass filter. More specifically, for example, in a shallow portion shallower than a focal depth of an ultrasonic beam, a signal of a low-frequency component equal to or lower than a predetermined lower limit value can be cut and an ultrasound image can be generated by only a signal of a high-frequency component. In a deep portion deeper than the focal depth of the ultrasonic beam, a signal of a high-frequency component equal to or higher than a predetermined upper limit value can be cut and an ultrasound image can be generated by only a signal of a low-frequency component.

Alternatively, for example, in a deep portion deeper than the focal depth of the ultrasonic beam, a signal of a high-frequency component can be gradually cut such that a proportion of a signal of a low-frequency component is greater as the depth is deeper.

In this way, the filter processing depending on the depth is executed on the reception data, whereby it is possible to obtain an ultrasound image having higher image quality regardless of a depth.

Embodiment 4

In the ultrasound transducer 1 in Embodiment 1, although a plurality of piezoelectric oscillators 3 have a constant thickness in the Y direction, the thickness may be changed depending on a position in the Y direction.

Figure 9:
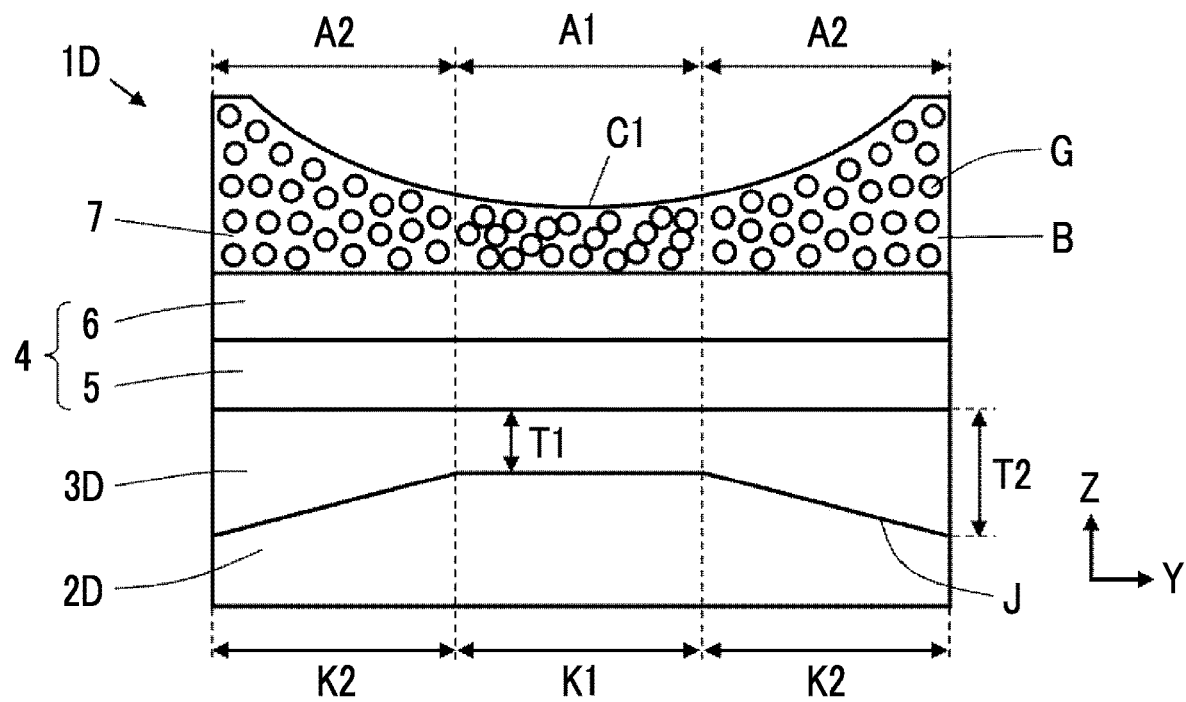
FIG. 9 is a sectional view of an ultrasound transducer in Embodiment 4 of the present invention.

As shown in FIG. 9, an ultrasound transducer 1D in Embodiment 4 of the present invention comprises a backing material 2D instead of the backing material 2 in the ultrasound transducer 1 in Embodiment 1 shown in FIGS. 1 and 2, and comprises a plurality of piezoelectric oscillators 3D instead of a plurality of piezoelectric oscillators 3.

The backing material 2D has a constant thickness in the central portion in the Y direction. In both end portions in the Y direction, the thickness of the backing material 2D is gradually thinner toward both end portions in the Y direction.

Each of a plurality of piezoelectric oscillators 3D includes a piezoelectric part K1 for a high frequency region having a constant thickness T1 in the central portion in the Y direction, and includes piezoelectric parts K2 for a low frequency region where the thickness of each piezoelectric oscillator 3D is thicker from the thickness T1 to a given thickness T2 from the central portion toward both end portions in the Y direction, in both end portions in the Y direction. The piezoelectric part K1 for a high frequency region is disposed at a position corresponding to the lens part A1 for a high acoustic velocity region of the acoustic lens 7 for an ultrasound transducer in the Y direction, and the piezoelectric parts K2 for a low frequency region are disposed at positions corresponding to the lens parts A2 for a low acoustic velocity region of the acoustic lens 7 for an ultrasound transducer in the Y direction. In an example shown in FIG. 9, each of the piezoelectric parts K2 for a low frequency region a plurality of piezoelectric oscillators 3D has an inclined surface portion J that is in contact with the backing material 2D and is inclined at a given slop to be further away from the acoustic matching layer 4 from the central portion toward both end portions in the Y direction.

Here, as the piezoelectric oscillator 3D is thicker, the transmission and reception frequency of the ultrasonic wave by the piezoelectric oscillator 3D is lower, and as the piezoelectric oscillator 3D is thinner, the transmission and reception frequency of the ultrasonic wave by the piezoelectric oscillator 3D is higher. Thus, the piezoelectric part K1 for a high frequency region transmits and receives a comparatively high-frequency ultrasonic wave, and the piezoelectric parts K2 for a low frequency region transmit and receive a comparatively low-frequency ultrasonic wave.

For this reason, the comparatively high-frequency ultrasonic waves emitted from the piezoelectric parts K1 for a high frequency region of a plurality of piezoelectric oscillators 3D propagate through the lens part A1 for a high acoustic velocity region of the acoustic lens 7 for an ultrasound transducer, and an ultrasonic beam formed from ultrasonic waves transmitted through the lens part A1 for a high acoustic velocity region has a narrow width in the Y direction and converges conforming to a comparatively short focal length F. The comparatively low-frequency ultrasonic waves emitted from the piezoelectric parts K2 for a low frequency region of a plurality of piezoelectric oscillators 3D propagates through the lens parts A2 for a low acoustic velocity region of the acoustic lens 7 for an ultrasound transducer, and an ultrasonic beam formed from the ultrasonic waves transmitted through the lens parts A2 for a low acoustic velocity region converges conforming to a comparatively long focal length F.

In this manner, with the ultrasound transducer 1D in Embodiment 4 of the present invention, each of a plurality of piezoelectric oscillators 3D is thicker from the central portion toward both end portions in the Y direction, whereby the transmission and reception frequency of the ultrasonic wave by each piezoelectric oscillator 3D is lower from the central portion toward both end portions in the Y direction. Thus, a comparatively high-frequency ultrasonic beam that has a narrow width in the Y direction converges in a shallow portion, and a comparatively low-frequency ultrasonic beam that is hardly attenuated converges in a deep portion. For this reason, it is possible to obtain an ultrasound image having high image quality regardless of a depth.

Although it has been shown that an aspect of Embodiment 4 is applied to the ultrasound transducer 1 in Embodiment 1, the aspect of Embodiment 4 can also be applied to the ultrasound transducer 1A in Embodiment 2 in the same manner. For example, as shown in FIG. 10, an ultrasound transducer 1E in a modification example of Embodiment 4 comprises the backing material 2D instead of the backing material 2 in the ultrasound transducer 1A shown in FIG. 6, and comprises a plurality of piezoelectric oscillators 3D instead of a plurality of piezoelectric oscillators 3.

In this case, the comparatively high-frequency ultrasonic waves emitted from the piezoelectric parts K1 for a high frequency region of a plurality of piezoelectric oscillators 3D propagate through the lens part A2 for a low acoustic velocity region of the acoustic lens 7A for an ultrasound transducer, and an ultrasonic beam formed from the ultrasonic waves transmitted through the lens part A2 for a low acoustic velocity region has a narrow width in the Y direction and converges conforming to a comparatively short focal length F. The comparatively low-frequency ultrasonic waves emitted from the piezoelectric parts K2 for a low frequency region of a plurality of piezoelectric oscillators 3D propagate through the lens parts A1 for a high acoustic velocity region of the acoustic lens 7A for an ultrasound transducer, and an ultrasonic beam formed from the ultrasonic waves transmitted through the lens parts A1 for a high acoustic velocity region converges conforming to a comparatively long focal length F.

In this way, with the ultrasound transducer 1E in the modification example of Embodiment 4 of the present invention, in the same manner as the ultrasound transducer 1D in Embodiment 4, it is possible to obtain an ultrasound image having higher image quality regardless of a depth.

Figure 10:
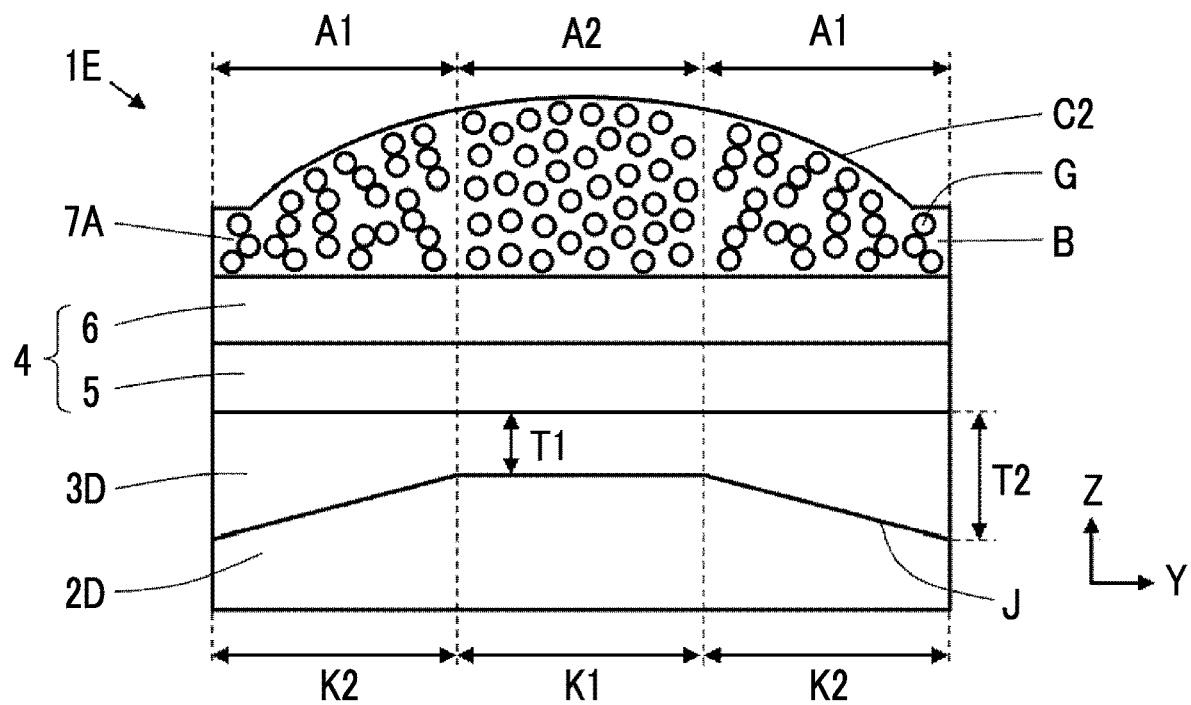
FIG. 10 is a sectional view of an ultrasound transducer in a modification example of Embodiment 4 of the present invention.

In FIGS. 9 and 10, although it has been shown that each of piezoelectric parts K2 for a low frequency region of a plurality of piezoelectric oscillators 3D has the inclined surface portion J that has the given slope and is inclined to be further away from the acoustic matching layer 4 from the central portion toward both end portions in the Y direction, the present disclosure is not particularly limited to this aspect as long as each a plurality of piezoelectric oscillators 3D is thicker from the central portion toward both end portions in the Y direction. Alternatively, for example, the slope of the inclined surface portion J may be gradually changed from the central portion toward both end portions in the Y direction such that the thickness of the piezoelectric part K2 for a low frequency region is gently changed from a thickness T1 to a thickness T2 from the central portion toward both end portions in the Y direction. For example, the piezoelectric part K2 for a low frequency region may have a planar portion (not shown) extending along the X direction and the Y direction instead of the inclined surface portion J to have a constant thickness T2 thicker than the thickness T1.

The length of the piezoelectric part K1 for a high frequency region in the Y direction is longer than the length of each of the piezoelectric parts K2 for a low frequency region in the Y direction, whereby it is possible to increase a proportion of comparatively high-frequency ultrasonic waves oscillated by a plurality of piezoelectric oscillators 3D. While ultrasonic waves having a higher frequency are more easily attenuated, the piezoelectric part K1 for a high frequency region is extended in the Y direction, whereby even though a comparatively high-frequency ultrasonic wave is attenuated in the subject, it is possible to sufficiently secure the amount of ultrasound echo that is received by the piezoelectric part K1 for a high frequency region, to restrain degradation of brightness of an ultrasound image of a comparatively shallow portion. With this, it is possible to obtain an ultrasound image having more uniform image quality.

In this case, for example, it is preferable that a length of the piezoelectric part K1 for a high frequency region in the Y direction is longer than ½ of a total length of the piezoelectric oscillator 3D in the Y direction. Specifically, for example, the length of the piezoelectric part K1 for a high frequency region in the Y direction may be two times or three times greater than a length of each of the piezoelectric parts K2 for a low frequency region in the Y direction.

Though not shown, the ultrasound diagnostic apparatus 11 having the ultrasound transducer 1D in Embodiment 4 or the ultrasound transducer 1E can comprise a so-called low-pass filter and a so-called high-pass filter, and can perform filter processing depending on a depth, for example, on reception data digitized by the AD conversion unit 25 using the low-pass filter and the high-pass filter. More specifically, for example, in a shallow portion shallower than a focal depth of an ultrasonic beam, a signal of a low-frequency component equal to or lower than a predetermined lower limit value can be cut and an ultrasound image can be generated by only a signal of a high-frequency component. In a deep portion deeper than the focal depth of the ultrasonic beam, a signal of a high-frequency component equal to or higher than a predetermined upper limit value can be cut and an ultrasound image can be generated by only a signal of a low-frequency component.

Alternatively, for example, in a deep portion deeper than the focal depth of the ultrasonic beam, a signal of a high-frequency component can be gradually cut such that a proportion of a signal of a low-frequency component is greater as the depth is deeper.

In this way, the filter processing depending on the depth is executed on the reception data, whereby it is possible to obtain an ultrasound image having higher image quality regardless of a depth.

An aspect of Embodiment 4 can also be applied to Embodiment 3 in the same manner as Embodiment 1 and Embodiment 2.

EXPLANATION OF REFERENCES 1, 1A, 1B, 1C, 1D, 1E: ultrasound transducer
2, 2D: backing material
3, 3D: piezoelectric oscillator
4, 4B: acoustic matching layer
5, 5B: first matching layer
6: second matching layer
7, 7A: acoustic lens for ultrasound transducer
8: separation portion
11: ultrasound diagnostic apparatus
12: transmission and reception circuit
13: image generation unit
14: display controller
15: monitor
16: apparatus controller
17: input device
21: ultrasound probe
22: processor
23: pulser
24: amplification unit
25: AD conversion unit
26: beam former
27: signal processing unit
28: DSC
29: image processing unit
A1: lens part for a high acoustic velocity region
A2: lens part for a low acoustic velocity region
B: base material
C1, C2: front surface
G: fine particles
H1: matching part for high frequency region
H2: matching part for low frequency region
K1: piezoelectric part for high frequency region
K2: piezoelectric part for low frequency region
P: arrangement pitch
T1, T2: thickness

What is claimed is:

1. An acoustic lens for an ultrasound transducer that is disposed in a front end portion of the ultrasound transducer,
   wherein the acoustic lens has a concave front surface,
   the acoustic lens is formed from a base material in which a plurality of fine particles are dispersed,
   a degree of dispersion of the plurality of fine particles is defined as an index representing uniformity of a distribution of the plurality of fine particles in the base material,
   the acoustic lens has a lens part for a high acoustic velocity region disposed in a central portion in an elevation direction and lens parts for a low acoustic velocity region disposed in both end portions in the elevation direction, where the degree of dispersion in the lens part for the high acoustic velocity region is lower than the degree of dispersion in the lens parts for the low acoustic velocity region.

2. The acoustic lens for the ultrasound transducer according to claim 1,
   wherein the front surface has the same curvature radius from the central portion to both end portions in the elevation direction.

3. The acoustic lens for the ultrasound transducer according to claim 1,
   wherein the number of fine particles per unit volume is the same from the central portion to both end portions in the elevation direction.

4. The acoustic lens for the ultrasound transducer according to claim 1,
   wherein the fine particles have a diameter equal to or greater than 0.01 μm and equal to or smaller than 100.00 μm.

5. The acoustic lens for the ultrasound transducer according to claim 4,
wherein the fine particles have a diameter equal to or greater than 1.00 μm and equal to or smaller than 10.00 μm.

6. The acoustic lens for the ultrasound transducer according to claim 1,
wherein the fine particles consist of iron, tungsten, alumina, zirconia, or silica.

7. An ultrasound transducer comprising:
a backing material;
a plurality of piezoelectric oscillators arranged and formed on a surface of the backing material;
an acoustic matching layer disposed on the plurality of piezoelectric oscillators; and
the acoustic lens according to claim 1 disposed on the acoustic matching layer.

8. The ultrasound transducer according to claim 7,
wherein the acoustic matching layer includes a first matching layer where a transmission and reception frequency of an ultrasonic wave is lower from the central portion toward both end portions in the elevation direction.

9. The ultrasound transducer according to claim 7,
wherein, as each of the plurality of piezoelectric oscillators is thicker from the central portion toward both end portions in the elevation direction, a transmission and reception frequency of an ultrasonic wave is lower from the central portion toward both end portions in the elevation direction.

10. An ultrasound probe comprising:
the ultrasound transducer according to claim 7.

11. An ultrasound diagnostic apparatus comprising:
the ultrasound probe according to claim 10.

12. An acoustic lens for an ultrasound transducer that is disposed in a front end portion of the ultrasound transducer,
wherein the acoustic lens has a convex front surface,
the acoustic lens is formed from a base material in which a plurality of fine particles are dispersed,
a degree of dispersion of the plurality of fine particles is defined as an index representing uniformity of a distribution of the plurality of fine particles in the base material, and
the acoustic lens has a lens part for a low acoustic velocity region disposed in a central portion in an elevation direction and lens parts for a high acoustic velocity region disposed in both end portions in the elevation direction, where the degree of dispersion in the lens part for the low acoustic velocity region is higher than the degree of dispersion in the lens parts for the high acoustic velocity region.

13. The acoustic lens for the ultrasound transducer according to claim 12,
wherein the front surface has the same curvature radius from the central portion to both end portions in the elevation direction.

14. The acoustic lens for the ultrasound transducer according to claim 12,
wherein the number of fine particles per unit volume is the same from the central portion to both end portions in the elevation direction.

* * * * *